(12) United States Patent
Abe et al.

(10) Patent No.: US 9,045,680 B2
(45) Date of Patent: Jun. 2, 2015

(54) IRIDIUM COMPLEX, ORGANIC LIGHT-EMITTING DEVICE, AND IMAGE DISPLAY APPARATUS

(75) Inventors: Shigemoto Abe, Yokohama (JP); Masashi Hashimoto, Tokyo (JP); Chiaki Nishiura, Kawasaki (JP); Hiroya Nitta, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 456 days.

(21) Appl. No.: 13/514,040

(22) PCT Filed: Nov. 26, 2010

(86) PCT No.: PCT/JP2010/071750
§ 371 (c)(1),
(2), (4) Date: Jun. 5, 2012

(87) PCT Pub. No.: WO2011/070987
PCT Pub. Date: Jun. 16, 2011

(65) Prior Publication Data
US 2012/0235135 A1 Sep. 20, 2012

(30) Foreign Application Priority Data
Dec. 8, 2009 (JP) ................................ 2009-278965

(51) Int. Cl.
| | | |
|---|---|---|
| *H01L 51/54* | (2006.01) | |
| *C09K 11/06* | (2006.01) | |
| *C07F 15/00* | (2006.01) | |
| *H05B 33/14* | (2006.01) | |
| *H01L 51/00* | (2006.01) | |
| *H01L 51/50* | (2006.01) | |

(52) U.S. Cl.
CPC ............ *C09K 11/06* (2013.01); *C07F 15/0033* (2013.01); *C09K 2211/1003* (2013.01); *C09K 2211/1044* (2013.01); *C09K 2211/1059* (2013.01); *C09K 2211/185* (2013.01); *H01L 51/0059* (2013.01); *H01L 51/0061* (2013.01); *H01L 51/0067* (2013.01); *H01L 51/0072* (2013.01); *H01L 51/0085* (2013.01); *H01L 51/5016* (2013.01); *H01L 2251/308* (2013.01); *H05B 33/14* (2013.01)

(58) Field of Classification Search
None
See application file for complete search history.

(56) References Cited

U.S. PATENT DOCUMENTS

2002/0034656 A1 * 3/2002 Thompson et al. .......... 428/690

FOREIGN PATENT DOCUMENTS

| | | |
|---|---|---|
| JP | 2007-51243 A | 3/2007 |
| JP | 2008-179617 A | 8/2008 |
| JP | 2009-96861 A | 5/2009 |
| WO | 2008078800 A | 7/2008 |
| WO | 2008/140115 A | 11/2008 |

OTHER PUBLICATIONS

Blue and near-UV phosphorescence from Iridium complexes with cyclometalated pyrazolyl or N-Heterocyclic carbene Ligands. (Sajoto, Tissa et al., Inorganic Chemistry, vol. 44, No. 22, pp. 7992-8003 (2005) ).

* cited by examiner

*Primary Examiner* — Marie R. Yamnitzky
(74) *Attorney, Agent, or Firm* — Canon U.S.A. Inc., IP Division

(57) ABSTRACT

There is provided a novel iridium complex having a small half-width of an emission spectrum and an organic light-emitting device that contains the iridium complex. There is provided a novel iridium complex that has a phenyl ring and a pyrazole ring as ligands and that has a basic skeleton in which the phenyl ring is bonded to a triazine ring.

9 Claims, 6 Drawing Sheets

FACIAL ISOMER  MERIDIONAL ISOMER

IRIDIUM COMPLEX, ORGANIC LIGHT-EMITTING DEVICE, AND IMAGE DISPLAY APPARATUS

TECHNICAL FIELD

The present invention relates to an iridium complex, an organic light-emitting device containing the iridium complex, and an image display apparatus containing the iridium complex.

BACKGROUND ART

Organic light-emitting devices are being actively developed. In the development of organic light-emitting devices, novel phosphorescent materials are being developed. Non-Patent Literature 1 describes an iridium complex having the following structural formula. Patent Literature 1 describes derivatives of this compound into which various substituents are introduced.

[Chem. 1]

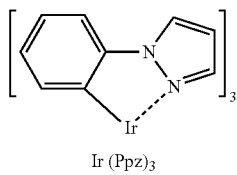

Ir (Ppz)$_3$

It is known that a compound having this structural formula, Ir(Ppz)$_3$, emits blue light at low temperatures but does not emit light at room temperature (Non-Patent Literature 1). Although derivatives of this compound into which various substituents are introduced are being studied, none of the derivatives have had desirable characteristics (Patent Literature 1).

CITATION LIST

Non Patent Literature

NPL 1 Blue and near-UV phosphorescence from iridium complexes with cyclometalated pyrazolyl or N-heterocyclic carbene ligands. (Sajoto, Tissa et al., Inorganic Chemistry, Vol. 44, No. 22, p. 7992 (2005))

Patent Literature

PTL 1 Japanese Patent Laid-Open No. 2007-051243

SUMMARY OF INVENTION

The present invention provides a novel iridium complex that has excellent light-emitting properties in a blue to green emission region. The present invention also provides an organic light-emitting device that contains the iridium complex and has excellent light-emitting properties.

The present invention provides an iridium complex having the following general formula (1):

[Chem. 2]

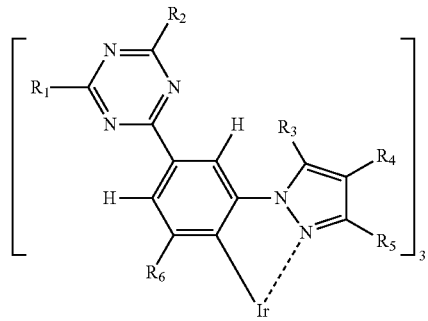

wherein H denotes a hydrogen atom, N denotes a nitrogen atom, Ir denotes an iridium atom,
R$_1$ and R$_2$ denote an alkyl group,
R$_3$, R$_4$, and R$_5$ are independently selected from a hydrogen atom and alkyl groups, and R$_6$ denotes a hydrogen atom or a cyano group.

DESCRIPTION OF EMBODIMENTS

Figure 1:
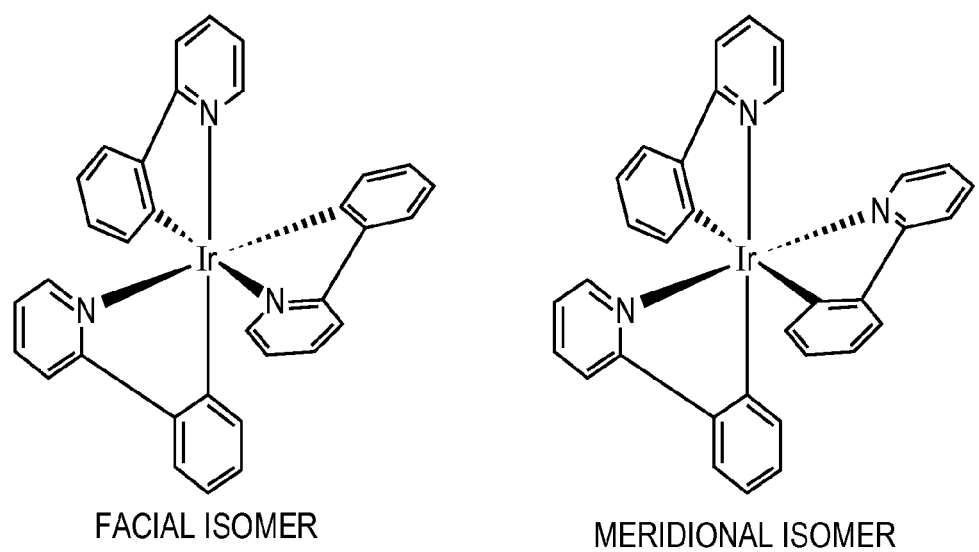
FIG. 1 illustrates stereoisomers that are of a prior art iridium complex.

An iridium complex according to one embodiment of the present invention has the following general formula (1):

[Chem. 3]

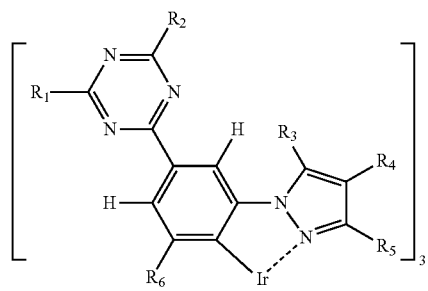

wherein H denotes a hydrogen atom, N denotes a nitrogen atom, Ir denotes an iridium atom, $R_1$ and $R_2$ denote an alkyl group, $R_3$, $R_4$, and $R_5$ are independently selected from a hydrogen atom and alkyl groups, and $R_6$ denotes a hydrogen atom or a cyano group.

As shown in the general formula (1), the iridium complex having the general formula (1) according to one embodiment of the present invention has a skeleton in which a triazine ring, a phenyl ring, and a pyrazole ring are bonded at particular positions. This skeleton is hereinafter referred to as "the main skeleton of a ligand having the general formula (1)".

The iridium complex according to one embodiment of the present invention is an excellent blue- or green-light-emitting complex because of a strong ligand field resulting from the main skeleton of a ligand having the general formula (1).

The ligand structure composed of the triazine ring, the phenyl ring, and the pyrazole ring may be one of the following four structures A to D. Among them, the structure C, that is, the main skeleton of a ligand having the general formula (1) is excellent as a basic skeleton of a light-emitting material particularly in a blue emission region.

[Chem. 4]

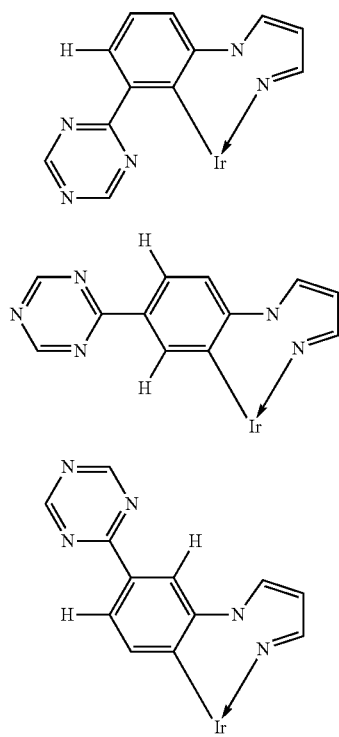

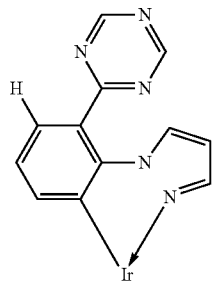

It is necessary to use a ligand that can form a stronger ligand field to achieve excellent light-emitting properties in blue and green emission regions. In general, it is important to increase m-back donation from a metal to a ligand to strengthen the ligand field. The present inventors found that the following two requirements are important to make the most of m-back donation resulting from the electron-withdrawing property of the triazine ring.

First requirement: The position of the triazine ring on the phenyl ring is ortho or para to iridium bonded to the phenyl ring.

Second requirement: The triazine ring and the phenyl ring can lie in the same plane.

The structure B does not meet the first requirement because the triazine ring on the phenyl ring is meta to iridium.

In the structures A and D, the triazine ring and the phenyl ring cannot lie in the same plane because of the steric repulsion between the triazine ring and a substituent on the phenyl ring disposed adjacent to the triazine ring, that is, the iridium atom in the structure A and the pyrazole ring in the structure D. Thus, the structures A and D cannot meet the second requirement.

Only the structure C meets the first requirement and the second requirement. Thus, the main skeleton of a ligand having the general formula (1) provides excellent light-emitting properties in a blue to green emission region, particularly in a blue emission region.

Thus, in order for the triazine ring and the phenyl ring to lie in the same plane, two hydrogen atoms Hs on the phenyl ring in the general formula (1) are important. The hydrogen atoms, which have a small van der Waals radius, have no steric repulsion or electronic repulsion with a nitrogen atom of the adjacent triazine ring. The iridium complex is most stable when the phenyl ring and the triazine ring lie in the same plane. The substitution of another atom or a substituent for these hydrogen atoms disposes the triazine ring and the phenyl ring in different planes because of steric repulsion and electronic repulsion.

The following table shows the dihedral angle between the triazine ring and the phenyl ring determined by molecular orbital calculation.

[Chem. 5]

| Compounds | | | |
|---|---|---|---|
| Dihedral angle | 0 degrees | 43 degrees | 50 degrees |

Thus, in order for the triazine ring and the phenyl ring to lie in the same plane, it is desirable that two hydrogen atoms be disposed at the positions of the phenyl ring adjacent to the triazine ring.

The dihedral angle was calculated by structural optimization calculation in the ground state using a commercially available electronic state calculation software, Gaussian 03* Revision D.01. The density functional theory was employed as quantum chemical calculation. B3LYP was used as a functional. In the Gaussian 03, Revision D.01, the basis function was 6-31G*.

* Gaussian 03, Revision D.01,
- M. J. Frisch, G. W. Trucks, H. B. Schlegel, G. E. Scuseria, M. A. Robb, J. R. Cheeseman, J. A. Montgomery, Jr., T. Vreven,
- K. N. Kudin, J. C. Burant, J. M. Millam, S. S. Iyengar, J. Tomasi,
- V. Barone, B. Mennucci, M. Cossi, G. Scalmani, N. Rega, G. A. Petersson, H. Nakatsuji, M. Hada, M. Ehara, K. Toyota,
- R. Fukuda, J. Hasegawa, M. Ishida, T. Nakajima, Y. Honda, O. Kitao,
- H. Nakai, M. Klene, X. Li, J. E. Knox, H. P. Hratchian, J. B. Cross,
- V. Bakken, C. Adamo, J. Jaramillo, R. Gomperts, R. E. Stratmann,
- O. Yazyev, A. J. Austin, R. Cammi, C. Pomelli, J. W. Ochterski,
- P. Y. Ayala, K. Morokuma, G. A. Voth, P. Salvador, J. J. Dannenberg,
- V. G. Zakrzewski, S. Dapprich, A. D. Daniels, M. C. Strain, O. Farkas, D. K. Malick, A. D. Rabuck, K. Raghavachari, J. B. Foresman, J. V. Ortiz, Q. Cui, A. G. Baboul, S. Clifford,
- J. Cioslowski, B. B. Stefanov, G. Liu, A. Liashenko, P. Piskorz,
- I. Komaromi, R. L. Martin, D. J. Fox, T. Keith, M. A. Al-Laham,
- C. Y. Peng, A. Nanayakkara, M. Challacombe, P. M. W. Gill,
- B. Johnson, W. Chen, M. W. Wong, C. Gonzalez, and J. A. Pople,
- Gaussian, Inc., Wallingford Conn., 2004.

Examples of the alkyl groups of $R_1$ and $R_2$ in the general formula (1) include, but are not limited to, a methyl group, an ethyl group, an iso-propyl group, a n-butyl group, an iso-butyl group, a sec-butyl group, a tert-butyl group, a neopentyl group, a cyclopropyl group, a cyclobutyl group, a cyclopentyl group, a cyclohexyl group, a bicyclo[2.2.2]octan-1-yl group, and a 1-adamantyl group. $R_1$ and $R_2$ may be the same or different. It is desirable that $R_1$ and $R_2$ be an alkyl group having a large excluded volume. An alkyl group having a large excluded volume can surround lone-pair electrons of the triazine ring to reduce the coordinating ability of the nitrogen atoms of the triazine ring. A specific substituent having a large excluded volume can effectively be a substituent containing a tertiary carbon having an $SP^3$ hybrid orbital, for example, a tert-butyl group, a bicyclo[2.2.2]octan-1-yl group, or a 1-adamantyl group.

The introduction of an alkyl group having a large excluded volume has at least one of the following effects.

Effect 1: A high-purity iridium complex can be produced in high yield.

Effect 2: Limited coordinating ability of the nitrogen atoms can prevent the lone-pair electrons from incorporating ionic impurities, thereby improving the life of an organic light-emitting device.

Effect 3: An alkyl group having a large excluded volume can reduce intermolecular interaction and the concentration quenching of a light-emitting material. The concentration quenching is a phenomenon in which the emission intensity decreases at high concentrations.

Examples of the alkyl groups of $R_3$, $R_4$, and $R_5$ include, but are not limited to, a methyl group, an ethyl group, a n-propyl group, an iso-propyl group, a n-butyl group, an iso-butyl group, a sec-butyl group, a tert-butyl group, a n-pentyl group, and a neopentyl group. $R_3$, $R_4$, and $R_5$ may be the same or different.

It is desirable that $R_3$, $R_4$, and $R_5$ be a hydrogen atom or a low-molecular-weight alkyl group in view of the purification of the complex. In order to change the luminescent color of the complex by altering the electronic state through electron donation, $R_5$ can effectively be an alkyl group, such as a methyl group or an ethyl group.

Since $R_6$ is close to the adjacent ligand, it is desirable that $R_6$ be a substituent having a small excluded volume, such as a hydrogen atom or a cyano group, to achieve a high synthesis yield of the complex. A cyano group is effective in increasing back donation from the metal to increase ligand field splitting.

An iridium complex according to one embodiment of the present invention can be used as a guest material or a host material for a light-emitting layer of an organic light-emitting device according to one embodiment of the present invention. An organic light-emitting device according to one embodiment of the present invention includes a pair of electrodes and a light-emitting layer between the electrodes. An organic light-emitting device according to one embodiment of the present invention may further include another layer.

An iridium complex according to one embodiment of the present invention can be appropriately used in layers other than the light-emitting layer, for example, a hole-injection layer, a hole-transport layer, a hole/exciton blocking layer, an electron-transport layer, and an electron-injection layer. Among the compounds constituting the light-emitting layer, the host material is a compound having the highest weight ratio, and the guest material is a compound having a lower weight ratio than the host material. An iridium complex according to one embodiment of the present invention can be used as a guest material for a light-emitting layer of an organic light-emitting device according to one embodiment of the present invention. In particular, it is desirable that an iridium complex according to one embodiment of the present invention be used as a guest material for a blue- or green-light-emitting device.

The introduction of a substituent into the basic skeleton of an iridium complex according to one embodiment of the present invention can alter the emission wavelength. Examples of the substituent that can alter the emission wavelength include, but are not limited to, alkyl groups and a cyano group.

When an iridium complex according to one embodiment of the present invention is used as the guest material for the light-emitting layer, it is desirable that the host material be a material having a higher LUMO level than the iridium complex, that is, a material having an energy level closer to the vacuum level. This is because an iridium complex according to one embodiment of the present invention has a low LUMO level and can accept electrons smoothly from the host material in the light-emitting layer. The LUMO level stands for the lowest unoccupied molecular orbital level. The HOMO level stands for the highest occupied molecular orbital level. The host material and the guest material will be further described later.

Iridium Complexes According to Embodiments of the Present Invention
Specific examples of the compound having the general formula (1) will be described below. However, the present invention is not limited to these examples.
[Chem. 6]
pp1-1
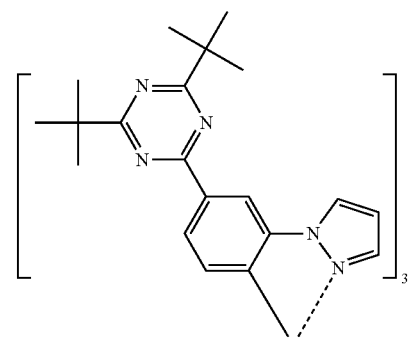
pp1-2
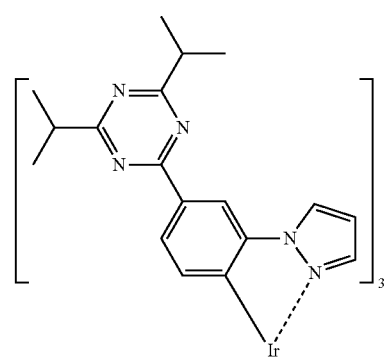
pp1-3
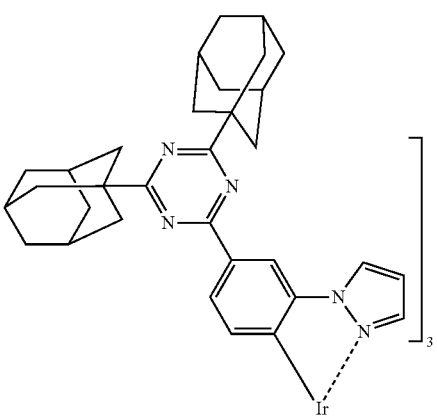
pp1-4
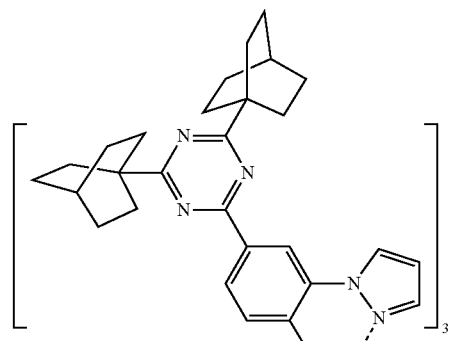
pp1-5
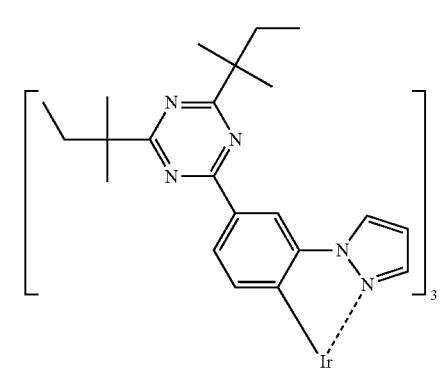
pp2-1
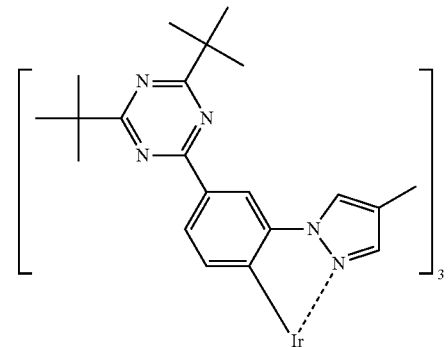
pp2-2
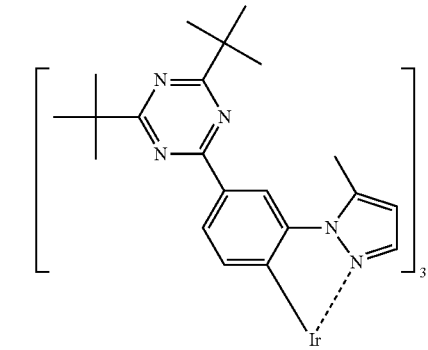

pp2-3
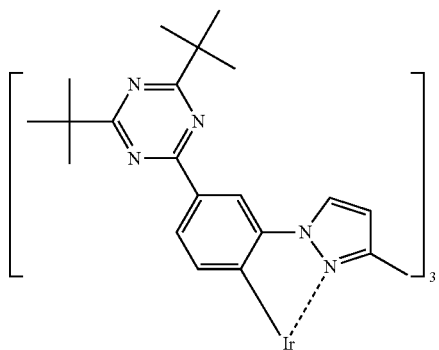
[Chem.7]
pp2-4
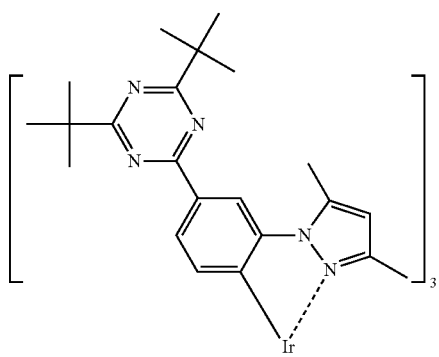
pp2-5
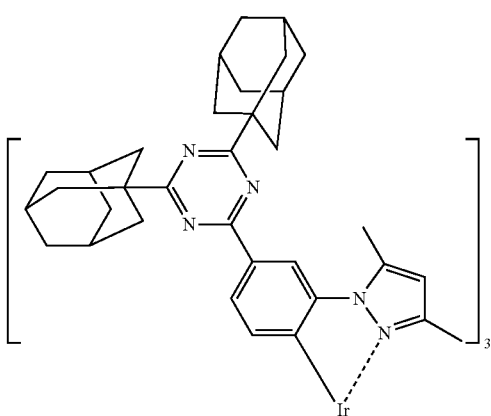
pp2-6
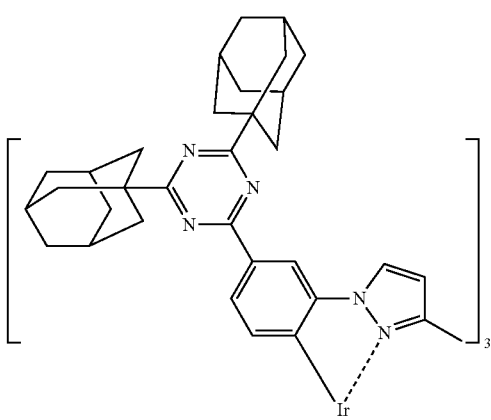
pp2-7
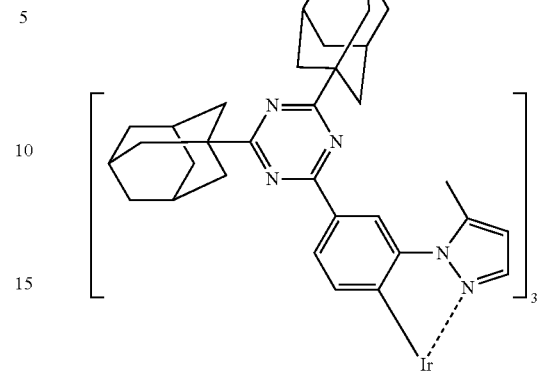
pp2-8
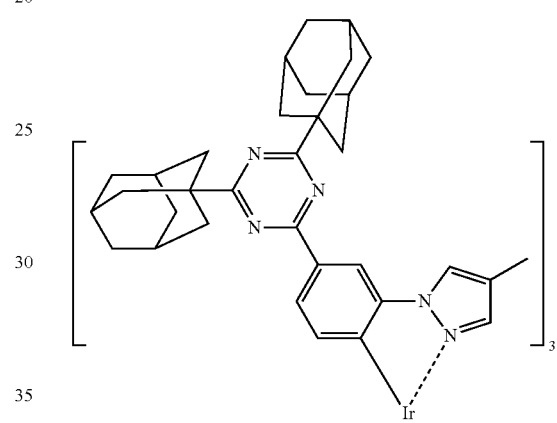
pp3-1
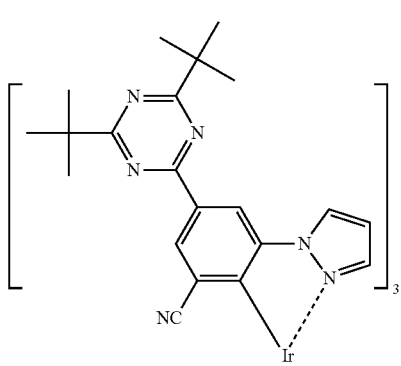
pp4-1
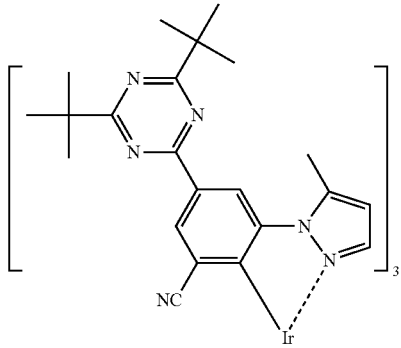

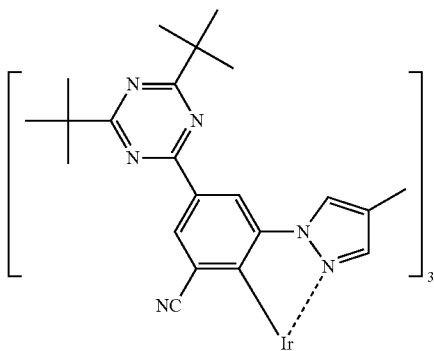

Iridium complexes according to embodiments of the present invention can be divided into the following four groups.

Group of pp11-1 to pp1-5

An Ir complex group that has an unsubstituted phenyl ring, an unsubstituted pyrazole ring, and substituents having a large excluded volume surrounding the lone-pair electrons of the triazine ring, the substituents corresponding to $R_1$ and $R_2$ of the general formula (1).

Group of pp2-1 to pp2-8

An Ir complex group in which an electron-donating group on the pyrazole ring alters the electronic state to allow the control of the maximum emission wavelength in the range of 450 to 500 nm.

Group of pp3-1

An Ir complex group in which an electron-withdrawing group on the phenyl ring increases back donation from the metal to increase the ligand field splitting width.

Group of pp4-1 to pp4-4

An Ir complex group in which an electron-withdrawing group on the phenyl ring and an electron-donating group on the pyrazole ring allow the control of the maximum emission wavelength in the range of 450 to 500 nm and increase the ligand field splitting width.

Exemplary compounds are described above. A substituent on the basic skeleton of an iridium complex according to one embodiment of the present invention allows light emission in the blue to green region.

Description of Synthetic Route

An example of a synthetic route to an iridium complex according to one embodiment of the present invention will be described below. The following are reaction formulae.

A ligand of an organic compound having the general formula (1) can be synthesized through the synthetic routes 1, 2, and 3 described below with reference to Angew. Chem. Int. Ed., (2008), Vol. 47, 8246-8250, Journal of Organic Chemistry, (2007), Vol. 72, 8535-8538, Japanese Patent Laid-Open No. 2008-0024698, and WO 2006/044821.

Various substituents are introduced in the literature described above. Thus, the ligand can be synthesized with the tert-butyl group being substituted with another substituent, such as a 1-adamantyl group. Likewise, a hydrogen atom can be substituted with another substituent, such as an alkyl group or a cyano group.

Synthetic Route 1

[Chem.8]

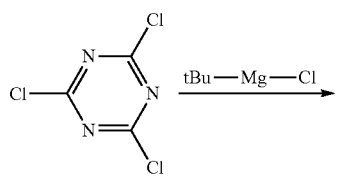

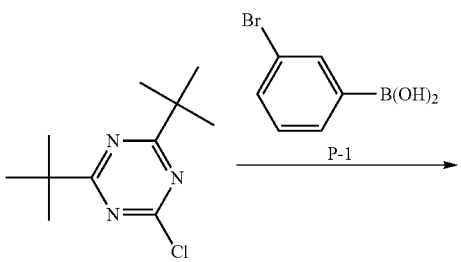

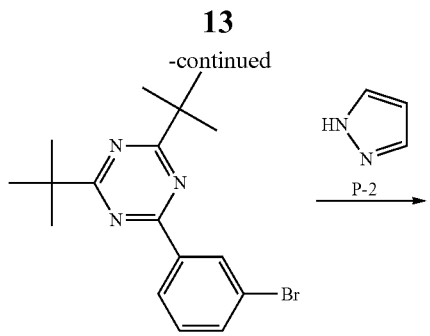
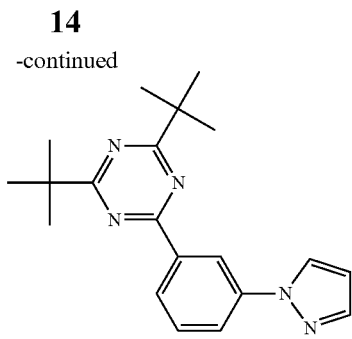
Synthetic Route 3
[Chem.10]
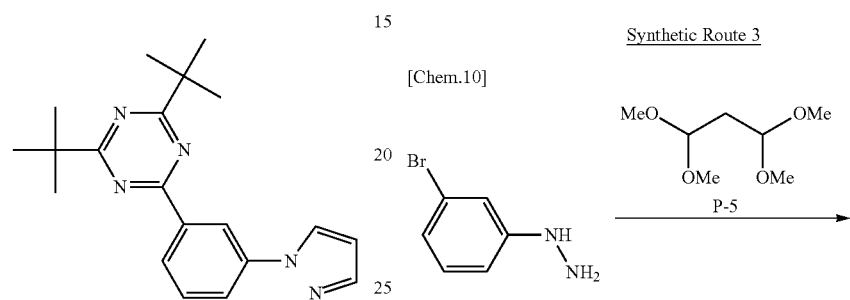
Synthetic Route 2
[Chem. 9]
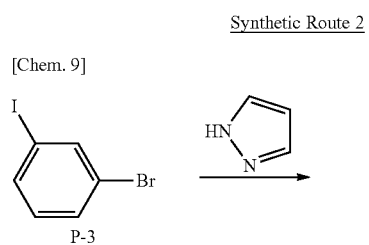
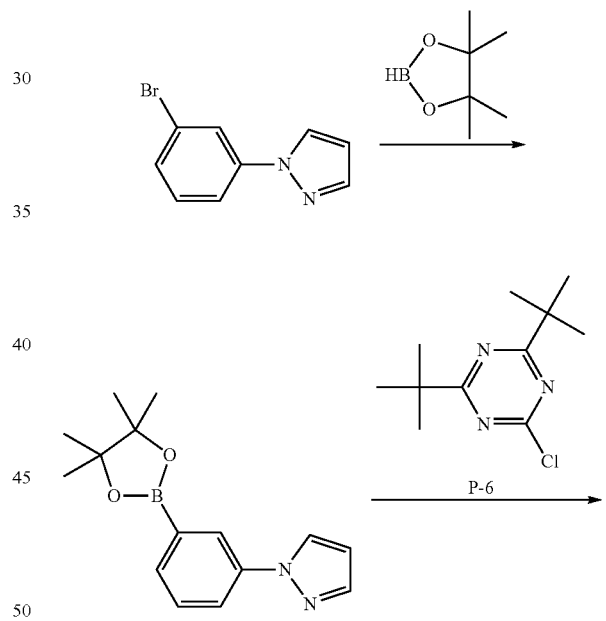
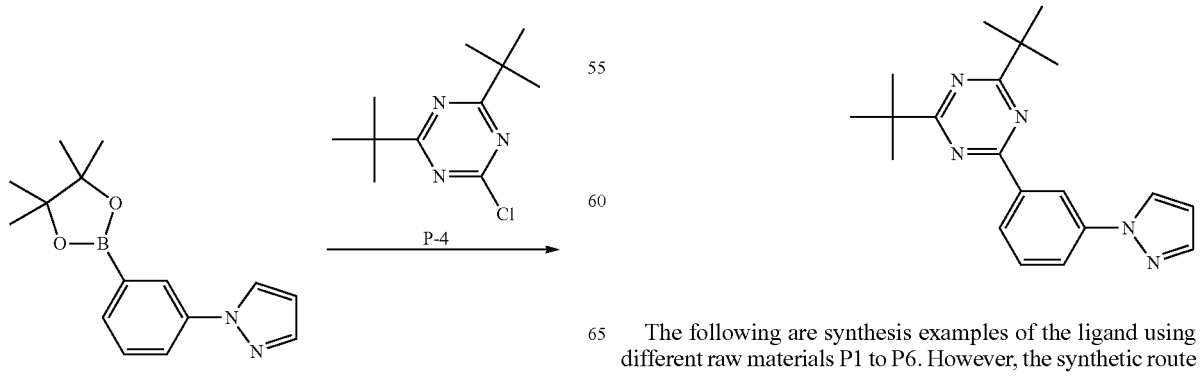
The following are synthesis examples of the ligand using different raw materials P1 to P6. However, the synthetic route is not limited to these synthesis examples.

[Chem. 11]
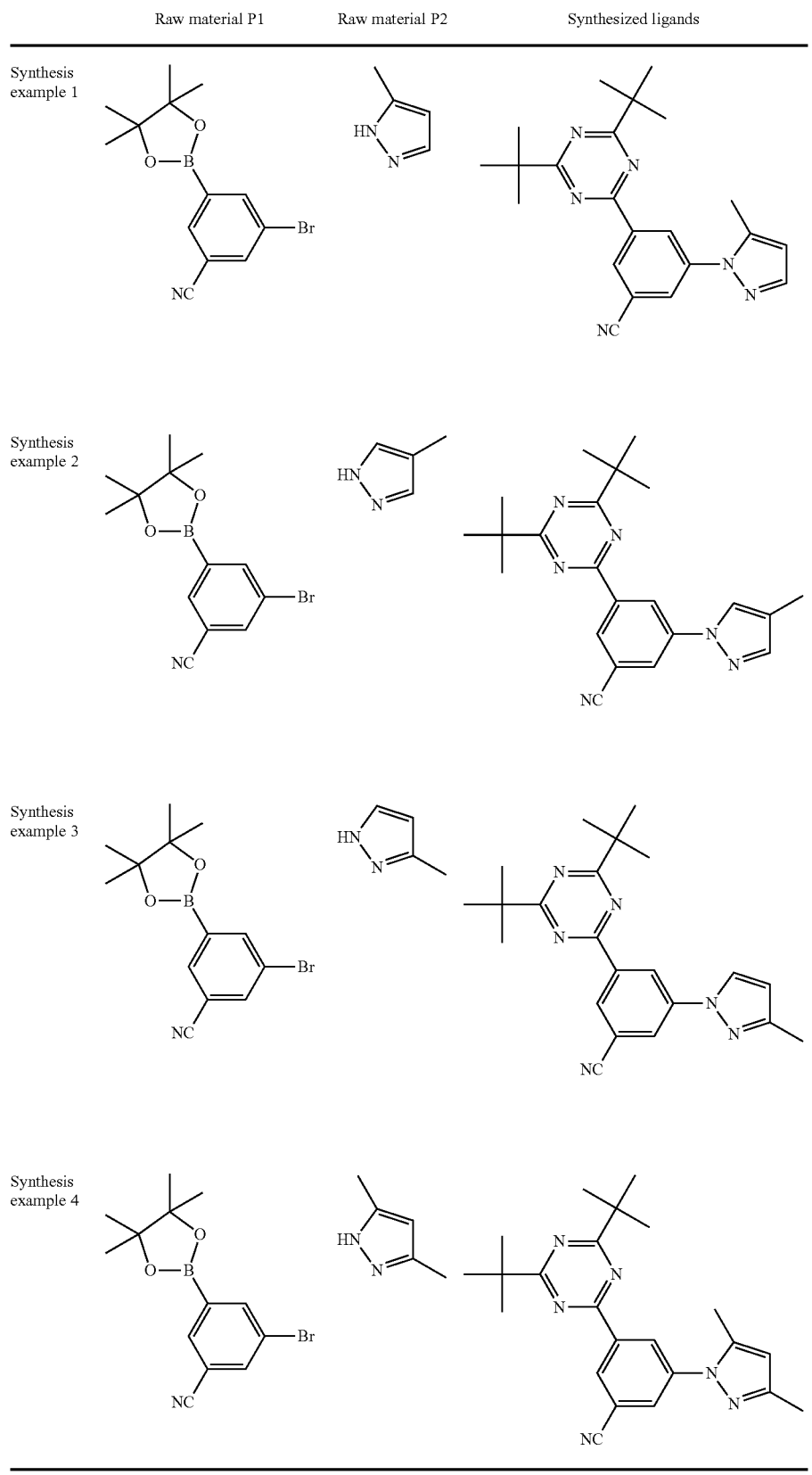

[Chem. 12]

| | Raw material P3 | Raw material P4 | Synthesized ligands |
|---|---|---|---|
| Synthesis example 5 | | | |
| Synthesis example 6 | | | |
| Synthesis example 7 | | | |
| Synthesis example 8 | | | |
| Synthesis example 9 | | | |

|  | Raw material P5 | Raw material P6 | Synthesized ligands |
|---|---|---|---|
| | | [Chem. 13] | |
| Synthesis example 10 | acetylacetone | 2,4-di-tert-butyl-6-chloro-1,3,5-triazine | 2-(di-tert-butyl)-6-[3-(3,5-dimethylpyrazol-1-yl)phenyl]-1,3,5-triazine |
| Synthesis example 11 | 4,4-dimethoxybutan-2-one | 2,4-di-tert-butyl-6-chloro-1,3,5-triazine | 2-(di-tert-butyl)-6-[3-(3-methylpyrazol-1-yl)phenyl]-1,3,5-triazine |
| Synthesis example 12 | S-methyl 3-oxobutanethioate | 2,4-di-tert-butyl-6-chloro-1,3,5-triazine | 2-(di-tert-butyl)-6-[3-(5-methylpyrazol-1-yl)phenyl]-1,3,5-triazine |
| Synthesis example 13 | 1,1,3,3-tetramethoxy-2-methylpropane | 2,4-di-tert-butyl-6-chloro-1,3,5-triazine | 2-(di-tert-butyl)-6-[3-(4-methylpyrazol-1-yl)phenyl]-1,3,5-triazine |
| | | [Chem. 14] | |
| Synthesis example 14 | acetylacetone | 2,4-di(adamantyl)-6-chloro-1,3,5-triazine | 2-(di-adamantyl)-6-[3-(3,5-dimethylpyrazol-1-yl)phenyl]-1,3,5-triazine |

| | Raw material P5 | Raw material P6 | Synthesized ligands |
|---|---|---|---|
| Synthesis example 15 | | | |
| Synthesis example 16 | | | |
| Synthesis example 17 | | | |
Various ligands thus synthesized can be used to synthesize complexes through the following synthetic routes 4, 5, and 6.
Synthetic Route 4
[Chem. 15]
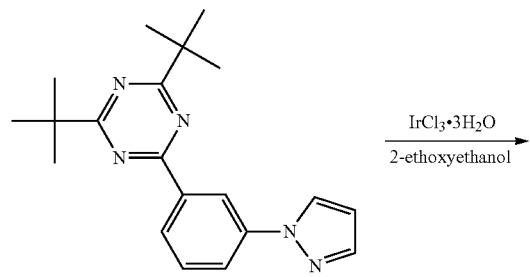

-continued
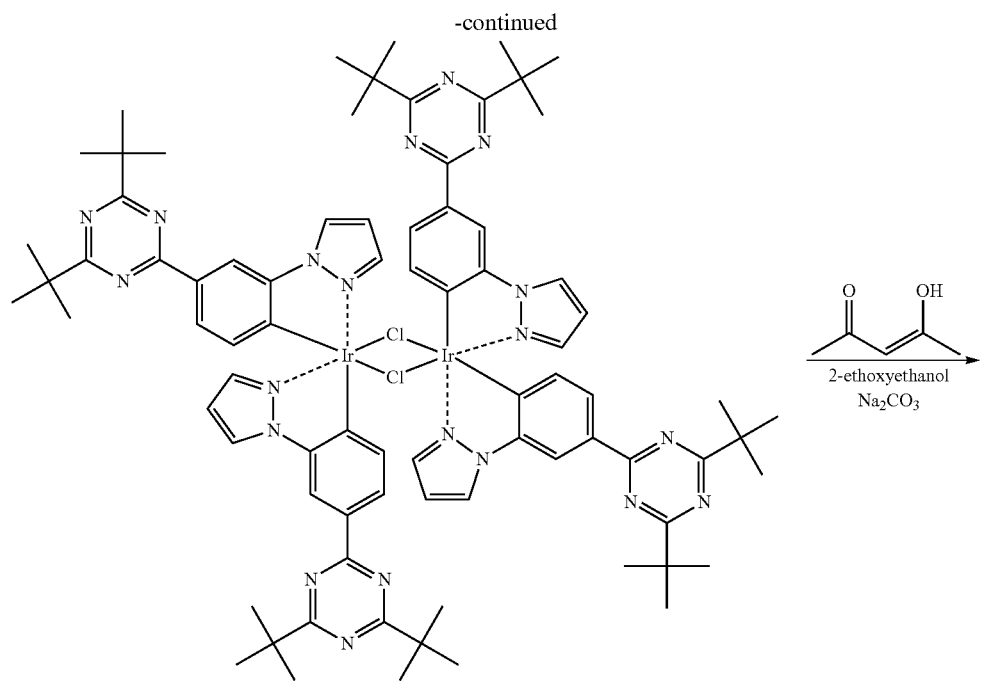
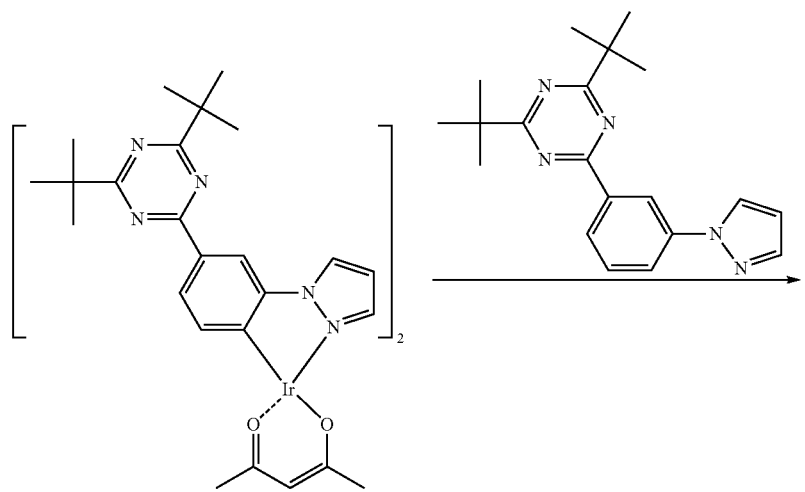
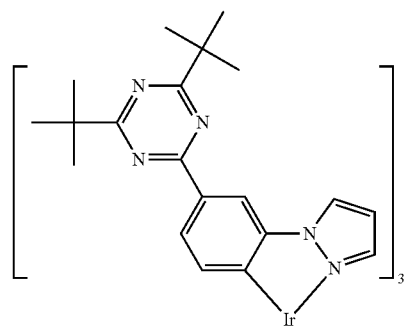

Synthetic Route 5

[Chem. 16]

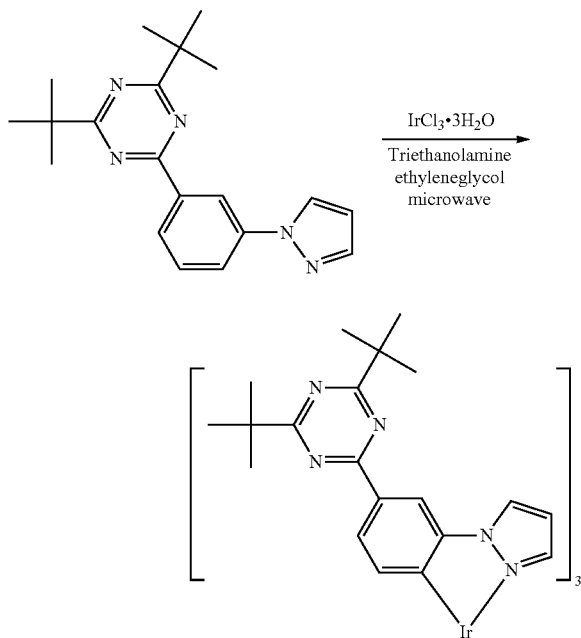

Synthetic Route 6

[Chem. 17]

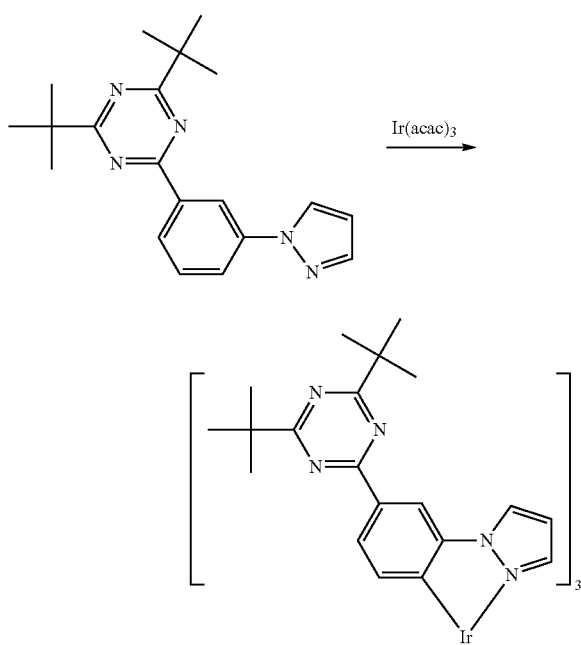

A complex synthesized by the synthetic route 4, 5, or 6 has a structural isomer: a facial isomer or a meridional isomer. In the synthesis of a complex, a meridional isomer may be the main product. FIG. 1 illustrates the facial isomer and the meridional isomer of Ir(ppy)$_3$. The facial isomer complex has better light-emitting properties and stability than the meridional isomer complex. Thus, it is desirable that the facial isomer be used as an Ir complex for an organic light-emitting device. The meridional isomer can be isomerized into the facial isomer. The facial isomer can therefore be produced by the isomerization of the meridional isomer. A method for producing the facial isomer by isomerization may be, but is not limited to, photoisomerization.

Description of Organic Light-Emitting Device

An organic light-emitting device according to one embodiment of the present invention will be described below.

An organic light-emitting device according to one embodiment of the present invention includes a pair of electrodes, an anode and a cathode, and an organic compound layer between the electrodes. The organic compound layer contains an iridium complex having the general formula (1). In the organic light-emitting device, carriers of the anode and the cathode are injected into the organic compound layer to produce an exciton of the light-emitting iridium complex. The organic light-emitting device emits light while the exciton returns to the ground state.

In the case that the organic compound layer functions as a light-emitting layer, the light-emitting layer may be formed only of an iridium complex according to one embodiment of the present invention or may contain another component.

When the light-emitting layer contains an iridium complex according to one embodiment of the present invention, the iridium complex may be the main component or an accessory component of the light-emitting layer.

The main component is a component having the highest weight ratio among the compounds constituting the light-emitting layer. An accessory component is a component having a lower weight ratio than the main component.

A material of the main component can also be referred to as a host material.

A material of an accessory component is a dopant (guest) material. Other accessory components include an emitting-assist material and a charge-injection material.

When an iridium complex according to one embodiment of the present invention is used as a guest material, the proportion of the guest material to the host material preferably ranges from 0.01% to 20% by weight, more preferably 0.5% to 10% by weight.

As a result of investigations, the present inventors found that a device that includes an iridium complex having the general formula (1) according to one embodiment of the present invention as a host material or a guest material, particularly a guest material, of a light-emitting layer can efficiently output high-intensity light and have high durability.

The following is an example of an organic light-emitting device that includes an iridium complex according to one embodiment of the present invention.

An organic light-emitting device that includes an iridium complex according to one embodiment of the present invention may include an anode, a light-emitting layer, and a cathode in this order on a substrate. Another organic light-emitting device that includes an iridium complex according to one embodiment of the present invention may include an anode, a hole-transport layer, an electron-transport layer, and a cathode in this order. In this case, since the interface between the hole-transport layer and the electron-transport layer emits light, the hole-transport layer and the electron-transport layer are considered as the light-emitting layers.

Still another organic light-emitting device that includes an iridium complex according to one embodiment of the present invention may include an anode, a hole-transport layer, a light-emitting layer, an electron-transport layer, and a cathode in this order. Still another organic light-emitting device that includes an iridium complex according to one embodiment of the present invention may include an anode, a hole-injection layer, a hole-transport layer, a light-emitting layer, an electron-transport layer, and a cathode in this order, or an anode, a hole-transport layer, a light-emitting layer, a hole/exciton blocking layer, an electron-transport layer, and a cathode in this order. These five multilayer organic light-emitting devices only have a basic structure. An organic light-emitting device that includes an iridium complex according to one embodiment of the present invention is not limited to these devices. For example, an insulating layer, an adhesive layer, or an interference layer may be disposed at an interface between an electrode and an organic compound layer. An electron-transport layer or a hole-transport layer may be formed of two sublayers having different ionization potentials.

An iridium complex having the general formula (1) according to one embodiment of the present invention may be used in an organic compound layer of a light-emitting device having any layer structure.

In addition to an iridium complex according to one embodiment of the present invention, another compound may be used if necessary. Examples of the other compound include, but are not limited to, a hole-injecting compound, a hole-transporting compound, a host compound, which is a host material, a light-emitting compound, an electron-injecting compound, and an electron-transporting compound. These compounds are conventionally known low- or high-molecular-weight compounds.

Examples of these compounds will be described below.

It is desirable that the hole-injecting compound and hole-transporting compound be materials having high hole mobility. Examples of the low- or high-molecular-weight material having hole-injection ability or hole-transport ability include triarylamine derivatives, phenylenediamine derivatives, stilbene derivatives, phthalocyanine derivatives, porphyrin derivatives, polyvinylcarbazole, polythiophene, and other electroconductive polymers.

The following table shows specific structural formulae of the host compounds. The host compounds may be derivatives of the compounds having structural formulae shown in the table. Other examples of the host compounds include, but are not limited to, fused-ring compounds (for example, fluorene derivatives, naphthalene derivatives, carbazole derivatives, quinoxaline derivatives, and quinoline derivatives), organic aluminum complexes, such as tris(8-quinolinolate)aluminum, organozinc complexes, triphenylamine derivatives, and polymer derivatives, such as polyfluorene derivatives and polyphenylene derivatives.

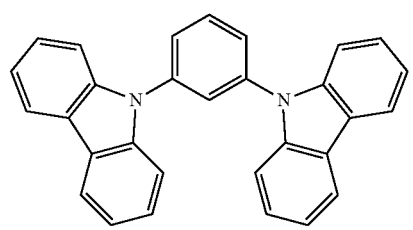

BH-01

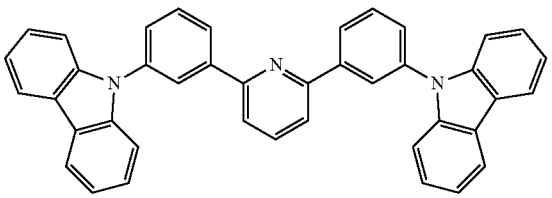

BH-02

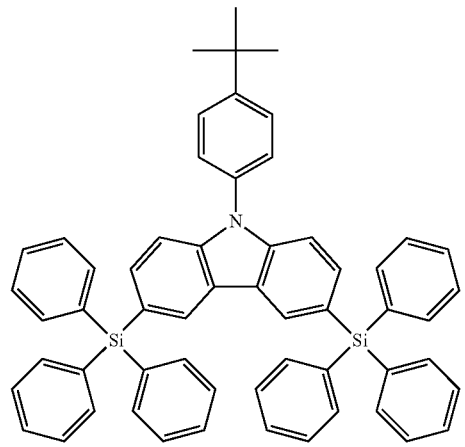

BH-03

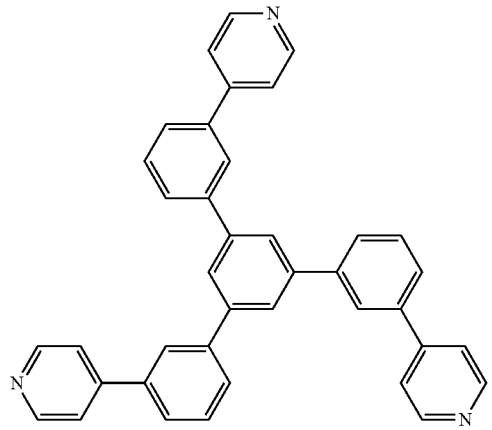

BH-04

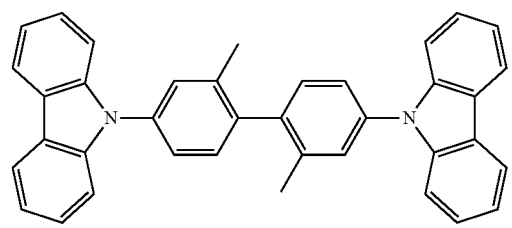

BH-05

BH-06

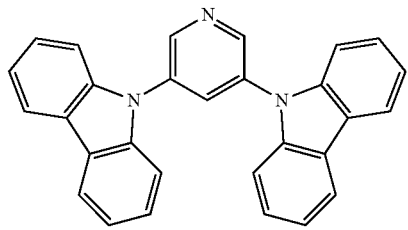

BH-07

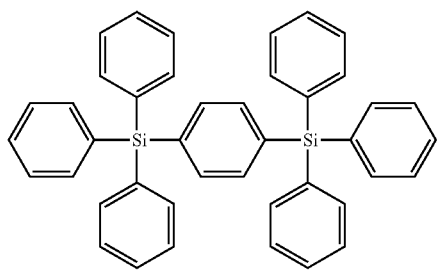

BH-08

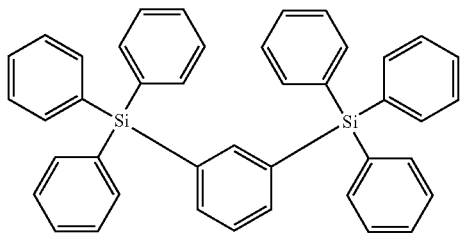

BH-09

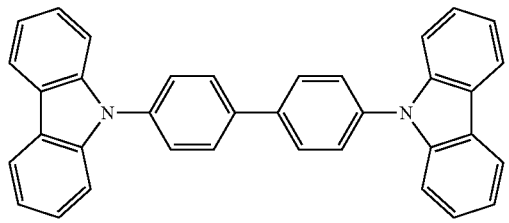

The electron-injecting compound or the electron-transporting compound is selected in consideration of balance with hole mobility of the hole-injecting compound or the hole-transporting compound. Examples of the compound having electron-injection ability or electron-transport ability include, but are not limited to, oxadiazole derivatives, oxazole derivatives, pyrazine derivatives, triazole derivatives, triazine derivatives, quinoline derivatives, quinoxaline derivatives, phenanthroline derivatives, and organic aluminum complexes.

It is desirable that the material for the anode have a work function as large as possible. Examples of the anode material include, but are not limited to, metallic elements, such as gold, platinum, silver, copper, nickel, palladium, cobalt, selenium, vanadium, and tungsten, alloys of these metallic elements, and metal oxides, such as tin oxide, zinc oxide, indium oxide, indium tin oxide (ITO), and indium zinc oxide. Examples of the anode material also include, but are not limited to, electroconductive polymers, such as polyaniline, polypyrrole, and polythiophene. These electrode substances may be used alone or in combination. The anode may have a monolayer or multilayer structure.

It is desirable that the material for the cathode have a work function as small as possible. Examples of the cathode material include, but are not limited to, alkali metals, such as lithium, alkaline-earth metals, such as calcium, and metallic elements, such as aluminum, titanium, manganese, silver, lead, and chromium. Examples of the cathode material also include, but are not limited to, alloys of these metallic elements, such as magnesium-silver, aluminum-lithium, and aluminum-magnesium. Metal oxides, such as indium tin oxide (ITO), may also be used. These electrode substances may be used alone or in combination. The cathode may have a monolayer or multilayer structure.

In an organic light-emitting device according to one embodiment of the present invention, a layer containing an iridium complex according to one embodiment of the present invention and a layer composed of another organic compound can be formed in the following manner. A thin film is generally formed by a vacuum evaporation method, an ionized deposition method, sputtering, plasma CVD, or a known coating method (for example, spin coating, dipping, casting, an LB method, or an ink jet method) using a solution in an appropriate solvent. A layer formed by a vacuum evaporation method or a solution coating method experiences little crystallization and has excellent temporal stability. In the film formation by a coating method, an iridium complex according to one embodiment of the present invention can be used in combination with an appropriate binder resin.

Examples of the binder resin include, but are not limited to, a polyvinylcarbazole resin, a polycarbonate resin, a polyester resin, an ABS resin, an acrylic resin, a polyimide resin, a phenolic resin, an epoxy resin, a silicone resin, and a urea resin. These binder resins may be used alone as a homopolymer or copolymer or in combination. If necessary, an additive agent, such as a known plasticizer, antioxidant, and/or ultraviolet absorber, may be used.

An organic light-emitting device according to one embodiment of the present invention can be used in display apparatuses and lighting apparatuses. An organic light-emitting device according to one embodiment of the present invention can also be used in exposure light sources of electrophotographic image-forming apparatuses and backlights of liquid crystal displays.

A display apparatus includes an organic light-emitting device according to one embodiment of the present invention in the display. The display includes pixels, which include an organic light-emitting device according to one embodiment of the present invention. The display apparatus can be used as an image display apparatus of PCs.

The display apparatus may be used in displays of image pickup devices, such as digital cameras and digital video cameras. Image pickup devices include the display and an image-capturing unit including an imaging optical system.

A display apparatus that includes an organic light-emitting device according to one embodiment of the present invention will be described below.

Figure 2:
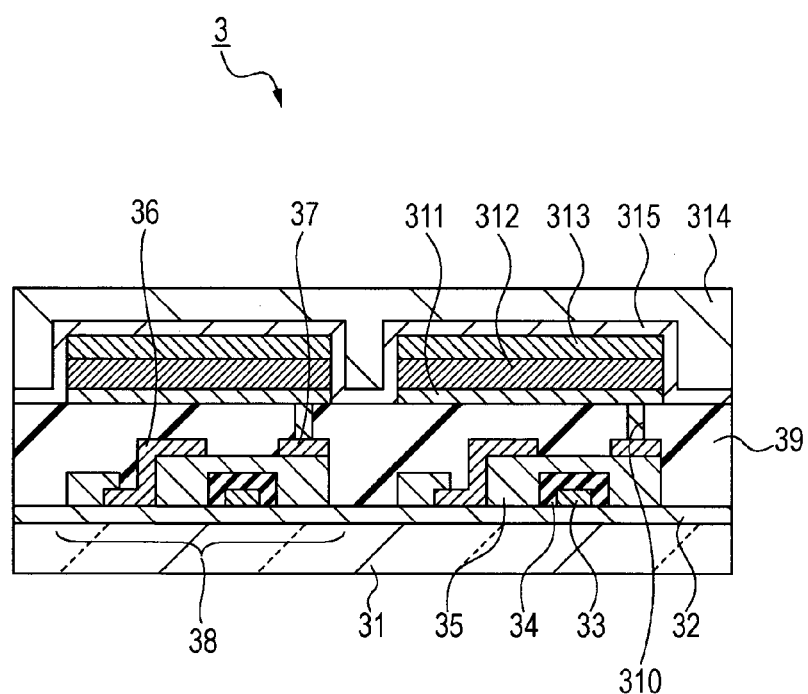
FIG. 2 is a schematic cross-sectional view of an organic light-emitting device and a TFT device, which is a switching device connected to the organic light-emitting device.

FIG. 2 is a schematic cross-sectional view of an organic light-emitting device according to one embodiment of the present invention and a switching device disposed on a substrate. The switching device drives the organic light-emitting device. The switching device is connected to the organic light-emitting device. This structure will be described in detail below.

A display apparatus 3 illustrated in FIG. 2 includes a substrate 31, for example, formed of glass, a moisture-proof film 32 for protecting a switching device TFT or an organic compound layer, a gate electrode 33, for example, formed of a metal, such as Cr, a gate-insulating film 34, and a semiconductor layer 35.

A TFT device 38 includes the semiconductor film 35, a drain electrode 36, and a source electrode 37. An insulating film 39 is disposed on the TFT device 38. An anode 311 of the organic light-emitting device is connected to the source electrode 37 through a contact hole (through hole) 310.

A multilayer organic compound layer 312 is illustrated as a single layer in FIG. 1. A first protective layer 314 and a second protective layer 315 for preventing degradation of the organic light-emitting device are disposed on a cathode 313.

The TFT device controls the luminance of the organic light-emitting device. A plurality of organic light-emitting devices on the substrate can emit light having their respective luminance to display images.

Although the TFT is described as the switching device in the present embodiment, a MIM device may also be used as the switching device.

A display apparatus that includes an organic light-emitting device according to one embodiment of the present invention can stably display high-quality images for a long period of time.

EXAMPLES

Although the present invention will be further described in the following examples, the present invention is not limited to these examples.

Example 1

Synthesis of Exemplary Compound pp1-1

[Chem. 19]

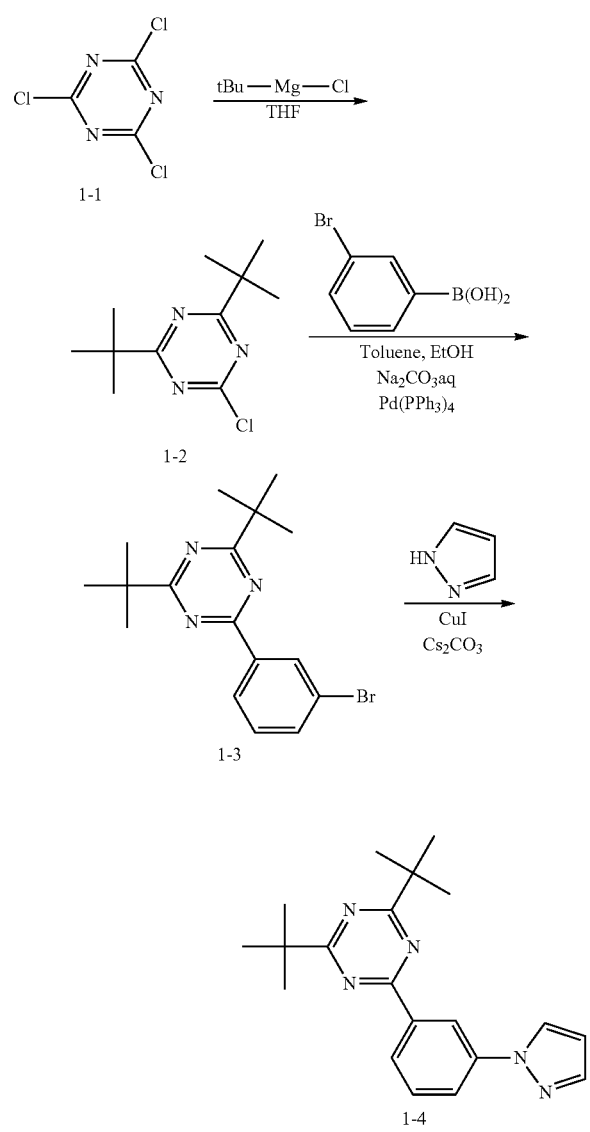

[Chem. 20]

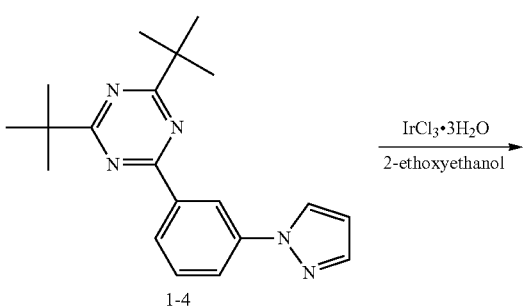

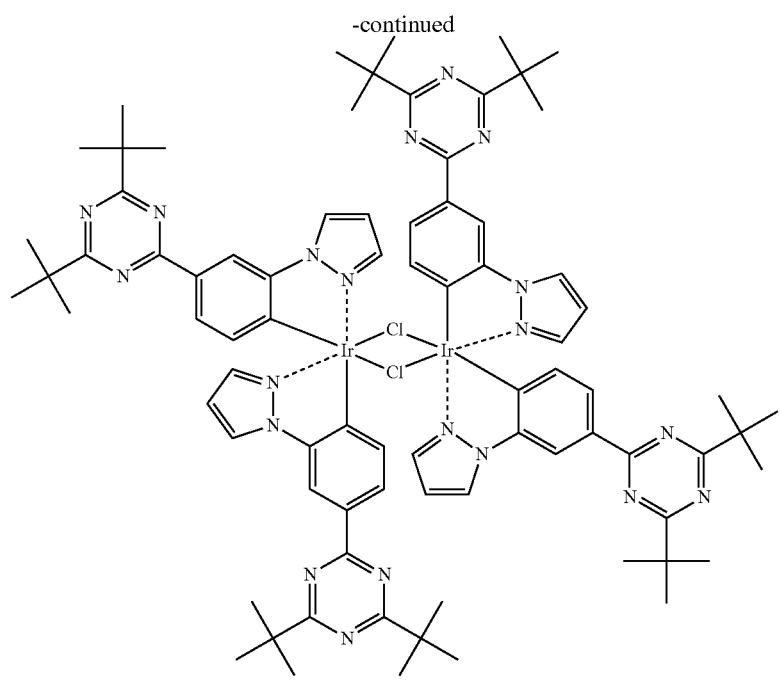
1-5
[Chem. 21]
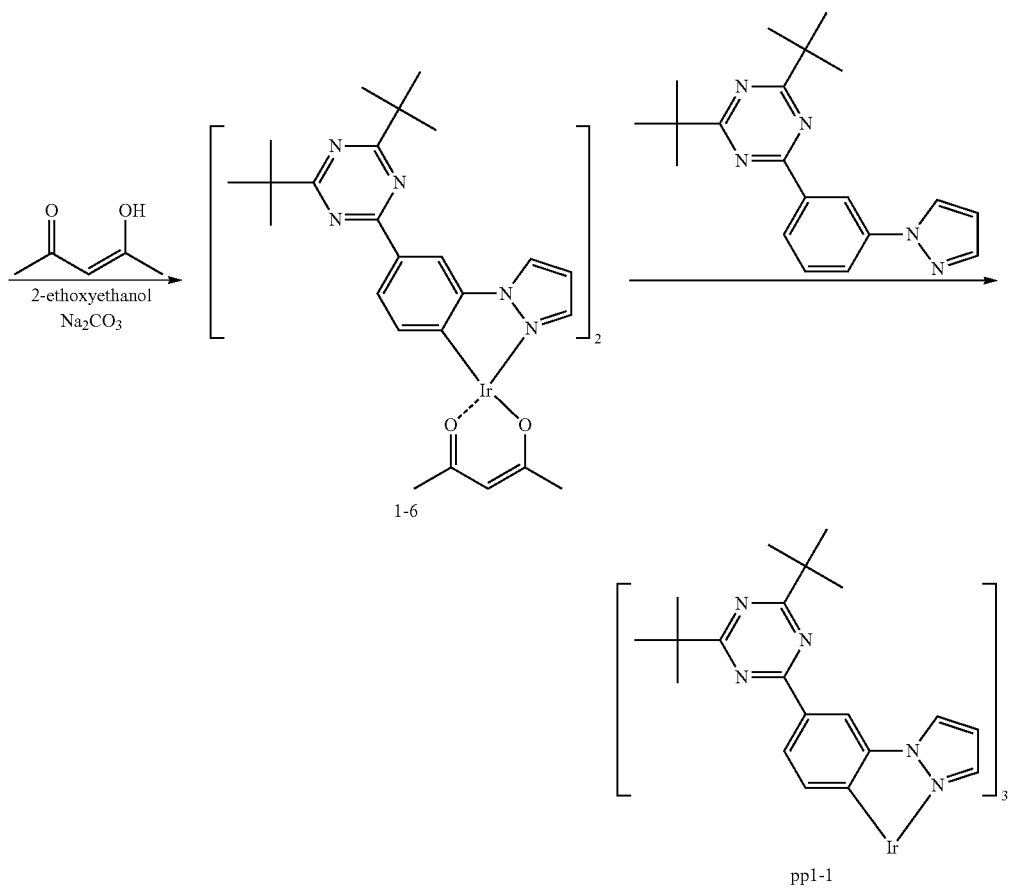

Synthesis of Intermediate 1-2

40.0 g (216.9 mmol) of a compound 1-1 and 1.5 g (7.88 mol) of copper (I) chloride were dissolved in 150 ml of dehydrated tetrahydrofuran. 210 ml (420.0 mmol) of tert-butylmagnesium chloride (23% tetrahydrofuran solution) was added dropwise to the solution at −5° C. After the completion of the addition, the solution was stirred at 0° C. for three hours. 30 ml of water was added to the solution. After the completion of the reaction, the solution was filtered through Celite. An organic layer was extracted with ethyl acetate, was dried over anhydrous sodium sulfate, and was concentrated. The concentrate was purified through a silica gel column (developing solvent: heptane/ethyl acetate=4/1) to produce 41.2 g (yield 83.3%) of a compound 1-2.

Synthesis of Intermediate 1-3

5.61 g (24.6 mmol) of the compound 1-2 and 4.50 g (22.4 mmol) of 3-bromophenylboronic acid were dissolved in a mixed solution of 70 ml of toluene, 35 ml of ethanol, and 35 ml of 2 N aqueous cesium carbonate. 1.73 g (1.49 mmol) of tetrakis(triphenylphosphine)palladium (0) was added to the solution in a nitrogen atmosphere at room temperature while stirring. The solution was heated to 70° C. and was stirred for five hours. After the completion of the reaction, an organic layer was extracted with toluene, was dried over anhydrous sodium sulfate, and was concentrated. The concentrate was purified through a silica gel column (developing solvent: heptane) to produce 6.80 g (yield 87.2%) of a compound 1-3.

Synthesis of Intermediate 1-4

6.20 g (17.8 mmol) of the compound 1-3, 1.70 g (24.9 mmol) of pyrazole, 0.68 g (3.56 mmol) of copper (I) iodide, and 11.6 g (35.6 mmol) of cesium carbonate were dissolved in 40 ml of dehydrated N,N-dimethylformamide. The solution was heated to 120° C. in a nitrogen atmosphere and was stirred for 12 hours. After the completion of the reaction, 100 ml of water was added to the solution. An organic layer was extracted with toluene, was dried over anhydrous sodium sulfate, and was concentrated. The concentrate was purified through a silica gel column (developing solvent: heptane/ethyl acetate=1/1) to produce 5.2 g (yield 87.1%) of a compound 1-4.

The structure of this compound was analyzed by $^1$H-NMR measurement (400 MHz, $CDCl_3$). σ (ppm): 8.83-8.82 (d, 1H), 8.54-8.52 (d, 1H), 8.05 (d, 1H), 7.95-7.93 (dd, 1H), 7.77 (s, 1H), 7.61-7.57 (t, 1H), 6.52-6.51 (t, 1H), 1.45 (s, 18H)

Synthesis of Intermediate 1-5

770 mg (2.30 mmol) of the compound 1-4 and 368 mg (1.04 mmol) of iridium (III) chloride hydrate were dissolved in 21 ml of 2-ethoxyethanol and 7 ml of water. The solution was heated to 110° C. in a nitrogen atmosphere and was stirred for 12 hours. After the completion of the reaction, 50 ml of water was added to the solution. A precipitated powder was filtered out by a membrane filter and was washed with water and methanol. The powder was dried to produce 830 mg (yield 44.5%) of a compound 1-5.

The structure of this compound was analyzed by $^1$H-NMR measurement (400 MHz, $CDCl_3$). σ (ppm): 8.38-8.37 (d, 4H), 8.33-8.32 (d, 4H), 7.94-7.93 (d, 4H), 7.79-7.77 (dd, 4H), 6.76-6.74 (t, 4H), 6.13-6.11 (d, 4H), 1.35 (s, 72H)

Synthesis of Intermediate 1-6

830 mg (0.46 mmol) of the compound 1-5, 2.0 g (20.2 mmol) of acetylacetone, and 1.7 g (16.0 mmol) of sodium carbonate were dissolved in 20 ml of 2-ethoxyethanol. The solution was heated to 95° C. in a nitrogen atmosphere and was stirred for five hours. After the completion of the reaction, 100 ml of water was added to the solution. A precipitated powder was filtered out by a membrane filter and was washed with water and methanol. The powder was dried to produce 880 mg (yield 99.6%) of a compound 1-6.

The structure of this compound was analyzed by $^1$H-NMR measurement (400 MHz, $CDCl_3$). σ (ppm): 8.33 (d, 2H), 8.26-8.25 (d, 2H), 7.88-7.85 (dd, 2H), 7.66-7.65 (d, 2H), 6.71-6.69 (t, 2H), 6.41-6.39 (d, 2H), 5.25 (s, 1H), 1.82 (s, 6H), 1.36 (s, 36H)

Synthesis of Compound pp1-1

500 mg (0.52 mmol) of the compound 1-6 and 1.05 g (3.12 mmol) of the compound 1-4 were heated to 220° C. in a nitrogen atmosphere and were stirred for 20 hours. After the completion of the reaction, the product was purified through a silica gel column (developing solvent: heptane/toluene=2/1) to produce 69 mg (yield 11.1%) of a meridional isomer of a compound pp1-1.

The structure of this compound was analyzed by $^1$H-NMR measurement (400 MHz, $CDCl_3$). σ (ppm): 8.50 (s, 1H), 8.45 (s, 1H), 8.41 (s, 1H), 8.23-8.22 (d, 1H), 8.19 (d, 1H), 8.15 (d, 1H), 8.13-8.12 (d, 1H), 8.10-8.08 (d, 1H), 8.05-8.03 (d, 1H), 7.24 (d, 1H), 7.19-7.18 (d, 1H), 7.08-7.07 (d, 1H), 6.97-6.95 (d, 1H), 6.87 (d, 1H), 6.64-6.62 (d, 1H), 6.44-6.42 (t, 2H), 6.40-6.39 (t, 1H), 1.40 (s, 18H), 1.40 (s, 18H), 1.39 (s, 18H)

Isomerization of Compound pp1-1

69 mg (0.058 mmol) of the meridional isomer of the compound pp1-1 was dissolved in 7 ml of N,N-dimethylformamide by heating in an argon atmosphere. The solution was irradiated with a 400 W medium-pressure mercury lamp for eight hours while the container was cooled with water. After the solution was concentrated, the residue was washed with methanol and was dried to produce 50 mg (yield 72.5%) of the facial isomer of the compound pp1-1.

The structure of this compound was analyzed by $^1$H-NMR measurement (400 MHz, $CDCl_3$). σ (ppm): 8.44 (s, 3H), 8.21-8.20 (d, 3H), 8.03-8.01 (dd, 3H), 7.06 (d, 3H), 7.06-7.04 (d, 3H), 6.46-6.45 (t, 3H), 1.40 (s, 54H)

The compound was identified by M+ at 1195 by matrix-assisted laser desorption ionization time-of-flight mass spectrometry (MALDI-TOF MS).

The light-emitting properties of the compound pp1-1 was compared with the light-emitting properties of $Ir(Ppz)_3$.

[Chem. 22]

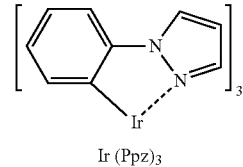

Ir (Ppz)$_3$

Figure 3:
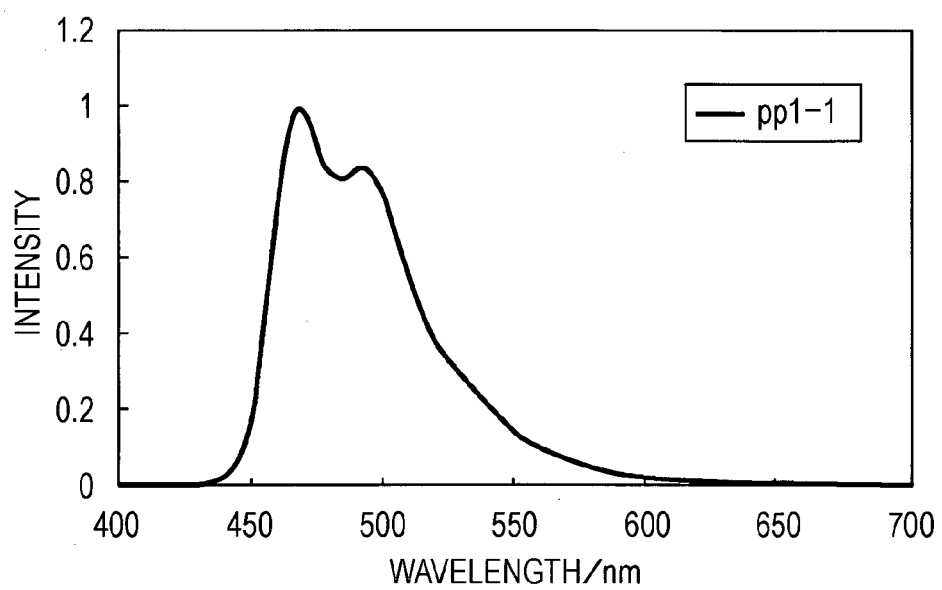
FIG. 3 shows the PL spectrum of a compound pp1-1 according to one embodiment of the present invention in toluene at room temperature.

The emission spectrum of a $1 \times 10^{-5}$ mol/l toluene solution of the compound pp1-1 was measured at room temperature by photoluminescence at an excitation wavelength of 350 nm with F-4500 manufactured by Hitachi, Ltd. (FIG. 3). In FIG. 3, the maximum intensity of the first peak was set at 1.0.

As shown in FIG. 3, the spectrum of the compound pp1-1 had the first peak having the maximum intensity at 468 nm and the second peak at 491 nm and had a half-width of 55 nm. The intensity of the second peak was 0.84 with the maximum intensity of the first peak being 1.0. No light emission was observed with the comparative compound Ir(Ppz)₃ under the same conditions.

Figure 4:
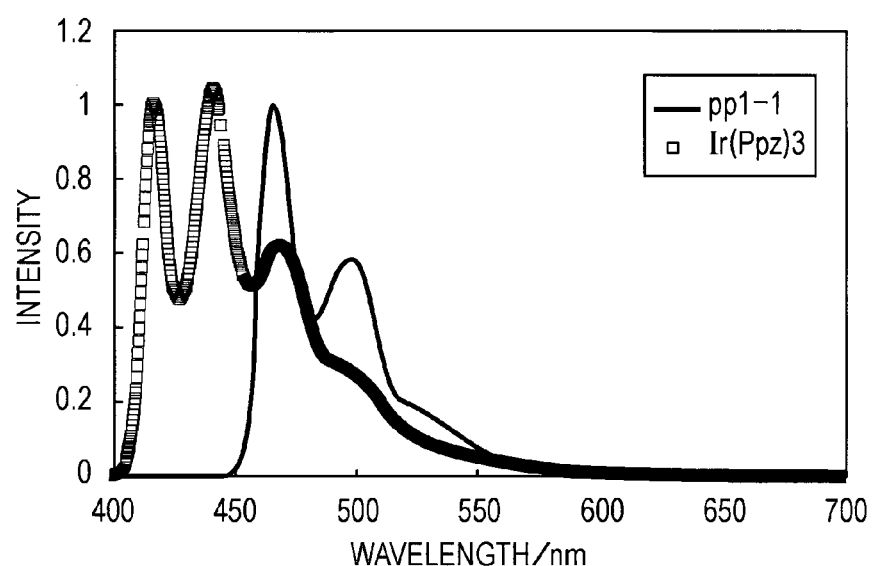
FIG. 4 shows the PL spectra of the compound pp1-1 according to one embodiment of the present invention and a reference example Ir(Ppz)$_3$ in toluene at a temperature of 77 K.

The emission spectrum of a 1×10⁻⁵ mol/1 toluene solution of the compound pp1-1 was measured at 77 K by photoluminescence at an excitation wavelength of 350 nm with F-4500 manufactured by Hitachi, Ltd. (FIG. 4). FIG. 4 also shows the PL measurement of Ir(Ppz)₃ under the same conditions as a comparative example. Two spectra were superposed with the intensity of the first peak being set at 1.0.

As shown in FIG. 4, the spectrum of the compound pp1-1 had the first peak having the maximum intensity at 466 nm and the second peak at 497 nm. The intensity of the second peak was 0.59 with the maximum intensity of the first peak being 1.0. The spectrum of the comparative compound Ir(Ppz)₃ had the first peak at 416 nm and the second peak having the maximum intensity at 441 nm. The intensity of the second peak was 1.05 with the intensity of the first peak being 1.0.

The absolute quantum yield of the compound pp1-1 in solution was determined to be 0.50 at room temperature with an absolute PL quantum yield measurement system (C9920-02) manufactured by Hamamatsu Photonics K.K.

The light-emitting properties of the compound pp1-1 was compared with the light-emitting properties of bIr-01 described below, which is a common blue-light-emitting complex having an emission wavelength close to the emission wavelength of the compound pp1-1.

[Chem. 23]

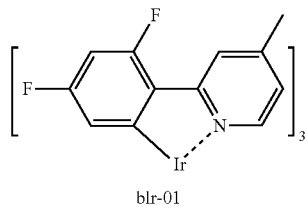

bIr-01

Figure 5:
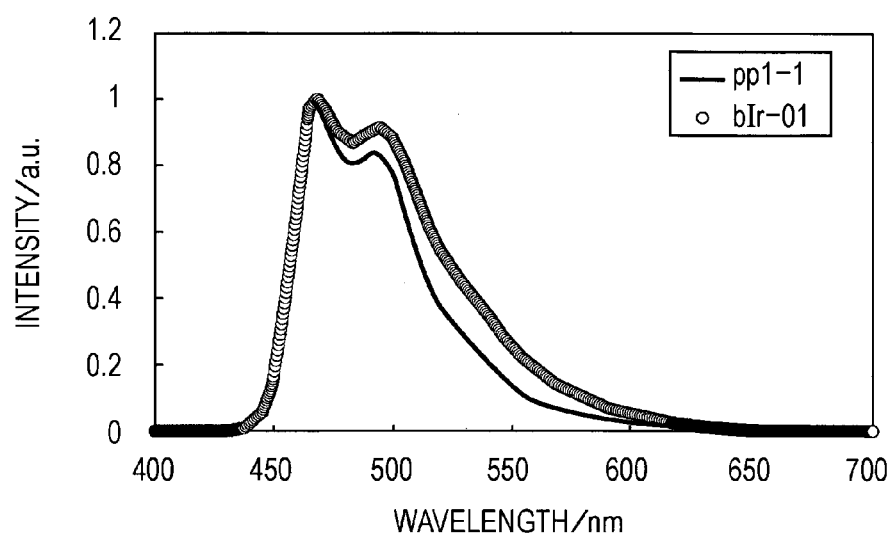
FIG. 5 shows the PL spectra of the compound pp1-1 according to one embodiment of the present invention and a reference example bIr-01 in toluene at room temperature.

The emission spectrum of a 1×10⁻⁵ mol/1 toluene solution of the compound pp1-1 was measured at room temperature by photoluminescence at an excitation wavelength of 350 nm with F-4500 manufactured by Hitachi, Ltd. (FIG. 5). FIG. 5 also shows the PL measurement of the blue-light-emitting homoleptic complex bIr-01 as a comparative example. Two spectra were superposed with the intensity of the first peak being set at 1.0.

As shown in FIG. 5, the spectrum of the compound pp1-1 had the first peak having the maximum intensity at 468 nm and the second peak at 491 nm and had a half-width of 55 nm. The intensity of the second peak was 0.84 with the maximum intensity of the first peak being 1.0. The spectrum of the comparative compound bIr-01 had the first peak having the maximum intensity at 468 nm and the second peak at 492 nm and had a half-width of 66 nm. The intensity of the second peak was 0.92 with the maximum intensity of the first peak being 1.0.

Figure 6:
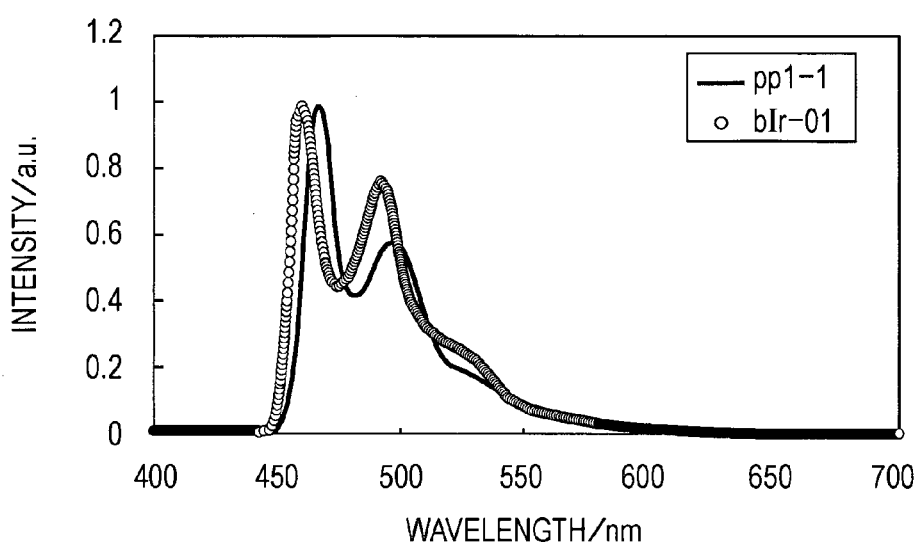
FIG. 6 shows the PL spectra of the compound pp1-1 according to one embodiment of the present invention and the reference example bIr-01 in toluene at a temperature of 77 K.

The emission spectrum of a 1×10⁻⁵ mol/1 toluene solution of the compound pp1-1 was measured at 77 K by photoluminescence at an excitation wavelength of 350 nm with F-4500 manufactured by Hitachi, Ltd. (FIG. 6). FIG. 6 also shows the PL measurement of bIr-01 under the same conditions as a comparative example. Two spectra were superposed with the intensity of the first peak being set at 1.0.

As shown in FIG. 6, the spectrum of the compound pp1-1 had the first peak having the maximum intensity at 466 nm and the second peak at 497 nm. The intensity of the second peak was 0.59 with the maximum intensity of the first peak being 1.0. The spectrum of the comparative compound bIr-01 had the first peak having the maximum intensity at 460 nm and the second peak at 492 nm. The intensity of the second peak was 0.77 with the maximum intensity of the first peak being 1.0.

These results show that the iridium complex according to the present example had a small half-width, a small second peak, and a high quantum yield. Thus, the iridium complex according to the present example is an excellent material for organic light-emitting devices.

Example 2

An organic light-emitting device was fabricated in the following manner.

An indium tin oxide (ITO) film having a thickness of 120 nm was formed as an anode on a glass substrate by sputtering. This substrate was used as a transparent electroconductive supporting substrate. The transparent electroconductive supporting substrate was subjected to ultrasonic cleaning in acetone and then isopropyl alcohol (IPA), was washed in boiled IPA, and was dried. The transparent electroconductive supporting substrate was then subjected to UV/ozone cleaning.

A 0.3% by weight chloroform solution of a compound 2-1 described below was spin-coated on the substrate at 1000 rpm for 40 seconds to form a hole-injection layer having a thickness of 30 nm. A compound 2-2 described below was then deposited by a vacuum evaporation method to form a hole-transport layer having a thickness of 20 nm. In the vacuum evaporation, the degree of vacuum was 1.0×10⁻⁴ Pa, and the deposition rate was 0.1 nm/sec.

A host compound 2-3 described below and a guest compound pp1-1 were co-evaporated on the hole-transport layer to form a light-emitting layer such that the compound pp1-1 content was 10% by weight of the total weight of the light-emitting layer. The light-emitting layer had a thickness of 40 nm. In the co-evaporation, the degree of vacuum was 1.0×10⁻⁴ Pa, and the deposition rate was 0.1 nm/sec.

A compound 2-4 described below was then deposited by a vacuum evaporation method to form an electron-transport layer having a thickness of 30 nm. In the vacuum evaporation, the degree of vacuum was 1.0×10⁻⁴ Pa, and the deposition rate ranged from 0.2 to 0.3 nm/sec.

A lithium fluoride film having a thickness of 0.5 nm was formed on the organic layer by a vacuum evaporation method. An aluminum film having a thickness of 150 nm was then formed by a vacuum evaporation method. Thus, an organic light-emitting device that included an aluminum-lithium alloy film as an electron-injection electrode (cathode) was fabricated. In the vacuum evaporation, the degree of vacuum was 1.0×10⁻⁴ Pa, and the deposition rate ranged from 1.0 to 1.2 nm/sec.

[Chem. 24]

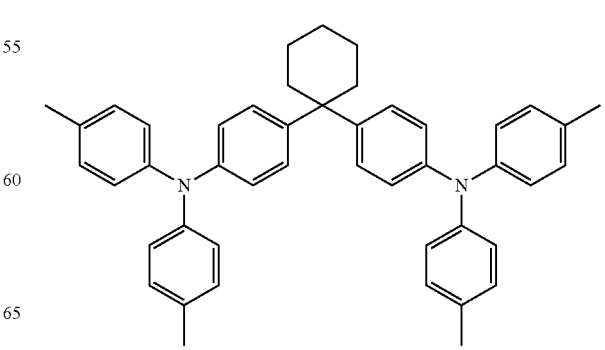

2-1

-continued

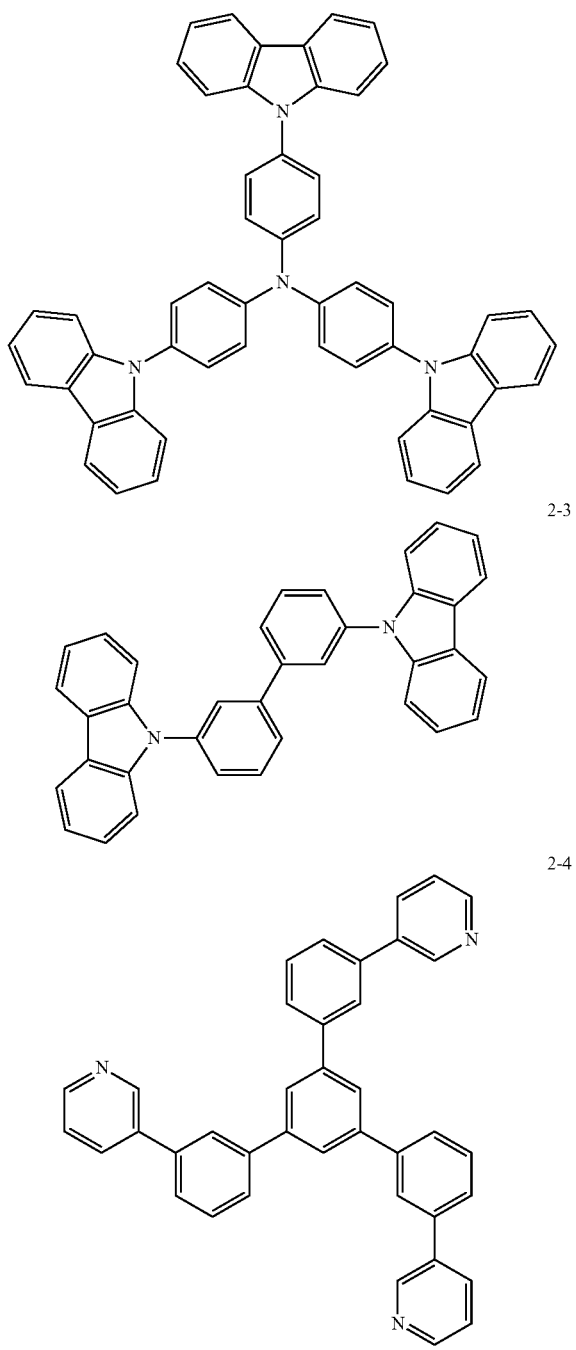

In order to prevent degradation caused by moisture adsorption, the organic light-emitting device was covered with a protective glass plate and was sealed with an acrylic resin binder in a dry air atmosphere.

The current-voltage characteristics of the organic light-emitting device thus fabricated were measured with a microammeter 4140B manufactured by Hewlett-Packard Co. using an ITO electrode (anode) as a positive electrode and an Al electrode (cathode) as a negative electrode. The luminance was measured with BM7 manufactured by Topcon Co. The luminance was 100 cd/m² at an applied voltage of 6.4 V. The external quantum efficiency ($\Phi_{exe}$) was 8.6%, indicating highly efficient emission. Blue light having a maximum wavelength of 474 nm and CIE chromaticity coordinates of (0.18, 0.36) was observed.

When a voltage was applied to the organic light-emitting device in a nitrogen atmosphere at an electric current density of 1 mA/cm², the luminance degradation after 10 hours was small.

Results and Discussion

An iridium complex according to the present invention is a novel compound that has a high quantum yield and excellent light-emitting properties in a blue to green emission region. An organic light-emitting device that contains the iridium complex has excellent light-emitting properties.

The embodiments and examples show that the present invention can provide a novel iridium complex having a small half-width of an emission spectrum. The present invention can also provide a novel iridium complex the emission wavelength of which can be altered by the introduction of a substituent into the basic skeleton of the iridium complex. The present invention can also provide an organic light-emitting device that contains any of the novel iridium complexes.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2009-278965, filed Dec. 8, 2009, which is hereby incorporated by reference herein in its entirety.

The invention claimed is:

1. An iridium complex having the following general formula (1):

[Chem. 1]

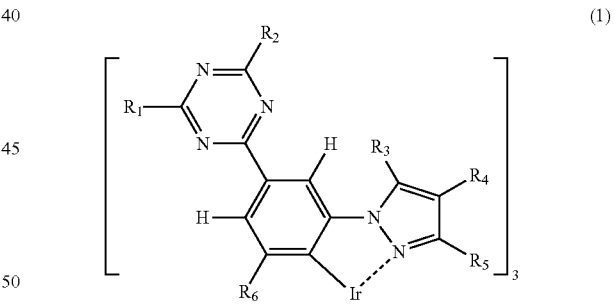

(1)

wherein H denotes a hydrogen atom, N denotes a nitrogen atom, Ir denotes an iridium atom, $R_1$ and $R_2$ denote an alkyl group, $R_3$, $R_4$, and $R_5$ are independently selected from a hydrogen atom and alkyl groups, and $R_6$ denotes a hydrogen atom or a cyano group.

2. The iridium complex according to claim 1, wherein $R_1$ and $R_2$ in the general formula (1) denote a tert-butyl group.

3. The iridium complex according to claim 2, wherein $R_6$ in the general formula (1) denotes a hydrogen atom.

4. An organic light-emitting device comprising:
a cathode;
an anode; and
an organic compound layer between the anode and the cathode, wherein the organic compound layer contains an iridium complex according to claim 1.

5. The organic light-emitting device according to claim 4, wherein the organic compound layer is a light-emitting layer.

6. An image display apparatus comprising a plurality of pixels, wherein each of the plurality of pixels includes an organic light-emitting device according to claim 4 and a switching device connected to the organic light-emitting device.

7. A lighting apparatus comprising the organic light-emitting device according to claim 4.

8. An electrophotographic image-forming apparatus comprising an exposure light source;
 wherein the exposure light source comprises the organic light-emitting device according to claim 4.

9. An exposure light source of an electrophotographic image-forming apparatus comprising the organic light-emitting device according to claim 4.

* * * * *